United States Patent [19]

Mouchel

[11] Patent Number: 5,034,009
[45] Date of Patent: Jul. 23, 1991

[54] INSTRUMENT FOR LOCATING THE PROXIMAL END OF THE URETHRA

[76] Inventor: Jack A. P. Mouchel, 16, rue Sainte-Croix, 72000 Le Mans, France

[21] Appl. No.: 397,043

[22] Filed: Aug. 22, 1989

[30] Foreign Application Priority Data

Nov. 3, 1987 [FR] France .................................. 87 15207

[51] Int. Cl.⁵ .............................................. B61B 17/00
[52] U.S. Cl. ......................................... 606/1; 128/778
[58] Field of Search .................... 128/774, 778; 606/1, 606/160; 33/836, 512; 604/280

[56] References Cited

U.S. PATENT DOCUMENTS

| | | | |
|---|---|---|---|
| 597,335 | 1/1898 | Spalding | 33/836 |
| 763,076 | 6/1904 | Spalding | 33/836 |
| 4,016,867 | 4/1977 | King . | |
| 4,121,572 | 10/1978 | Krzeminski | 33/836 |
| 4,281,462 | 8/1981 | Herbold . | |
| 4,500,313 | 2/1985 | Young . | |

FOREIGN PATENT DOCUMENTS 2100382 7/1970 France .
0019585 of 1904 United Kingdom ................ 33/836

OTHER PUBLICATIONS

Medical & Biological Engineering & Comput., vol. 18, No. 4, Jul. 1980, pp. 464–466, IEMBE, Stevenage, GB; A. N. Beard et al., "'Elastic Length' of the Female Uretha—Initial Measurements".

Primary Examiner—C. Fred Rosenbaum
Assistant Examiner—William W. Lewis
Attorney, Agent, or Firm—Eckert Seamans Cherin & Mellott

[57] ABSTRACT

This instrument for locating the proximal end of the urethra, comprises a graduated measuring rod, a cursor mounted so as to slide on the rod and means for locking of the cursor onto the rod.

5 Claims, 1 Drawing Sheet

INSTRUMENT FOR LOCATING THE PROXIMAL END OF THE URETHRA

BACKGROUND OF THE INVENTION

1. Field of the Invention

This invention relates to the instruments used for the surgical treatment of incontinence in women.

2. Prior Art

This treatment consists of making the vesico-urethral junction stronger by the fitting of the means of retention.

The vesico-urethral junction is located by inserting a small balloon through the urethra into the bladder, by inflating the small balloon fitted with a duct, by pulling it towards the meatus by means of this duct until it comes onto the neck of the bladder. The distal dome of the balloon is considered to correspond to the vesico-urethral junction.

In fact, it is nothing of the sort. Urinary incontinence is due to the softening and to the deformation of the tissues of the vesico-urethral junction. These tissues become deformed under the thrust from the balloon. The position of the neck determined in this way is offset towards the urethra with respect to the original vesico-urethral junction or anatomical junction (if the tissues had not yet yielded) by an unknown length, variable according to whether the balloon engages to a greater or lesser extent in the vesico-urethral funnel, depending on the quality of the tissues and on the traction force applied to the balloon.

SUMMARY OF THE INVENTION

The invention alleviates this disadvantage through an instrument which, combined with a process for measuring the length of the urethra other than the process utilising a small balloon, enables the vesico-urethral junction to be located, it having a been determined with less error.

The instrument according to the invention, for locating the proximal end of the urethra, is characterised in that it comprises a graduated measuring rod and a cursor mounted so as to slide on the rod.

The surgeon first determines the functional length of the urethra, i.e. the effective length of the urethra when the tissues are deformed, by a urodynamic exploration which consists essentially of plotting the curve of pressure variation along the urethra. The experiment shows that the functional length of the uretha, corresponding to the length of the urethra determined on this curve by the presence of a pressure, is in general less than the anatomical length by 8 mm, since there is no specific pressure in these last 8 mm of the urethra. The surgeon determines the anatomical length by adding 8 mm to the functional length. He puts the cursor on the graduated rod at a distance from one of the ends of the latter corresponding to the anatomical length. He inserts the instrument into the urethra through this end, until the cursor, which advantageously comprises a hilt for this purpose, comes into contact with the meatus. The said end of the rod indicates to him the location of the anatomical vesico-urethral junction. He performs the required surgical operation there.

In order to make this end of the rod more apparent to the surgeon during the operation, the end is advantageously angled.

The rod preferably comprises two opposed flats. This enables the cursor to be caused to slide even on the angled part, without jamming. This also enables it to be arranged for the cursor to be able to slide, but with a certain friction so that it does not move by itself. As need be, a device may be provided for locking the cursor in a given position on the rod.

BRIEF DESCRIPTION OF THE DRAWINGS

In the attached drawing, given solely by way of example.

DETAILED DESCRIPTION OF THE PREFERRED EMBODIMENTS

Figure 1:
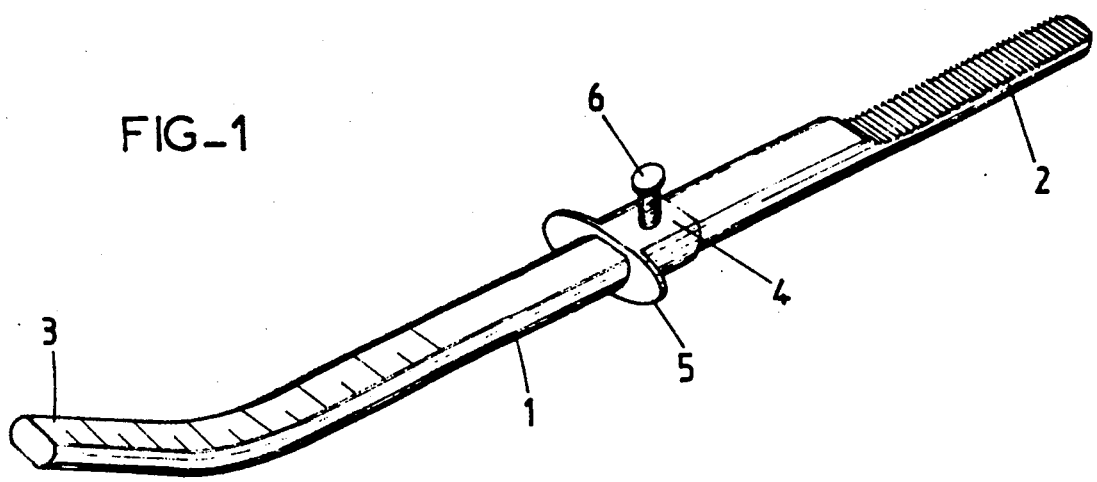
FIG. 1 is a perspective view of the instrument according to the invention.

The instrument comprises a graduated rod 1, fitted with a handle 2 at one of its ends. The other end 3 is set at a slight angle, less than 20°. A cursor 4 having a hilt 5 slides on the rod 1. A screw 6 enables the cursor 4 to be locked onto the rod 1.

Figure 2:
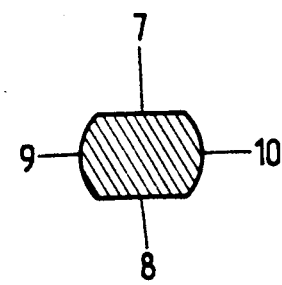
FIG. 2 is a cross-sectional view of the rod.

The rod 1 comprises two opposed flattened faces 7, 8 connected by two rounded faces 9 (FIG. 2). The dimensions of the straight section (5×5 mm approximately) enable it to be inserted into the urethra.

Figure 3:
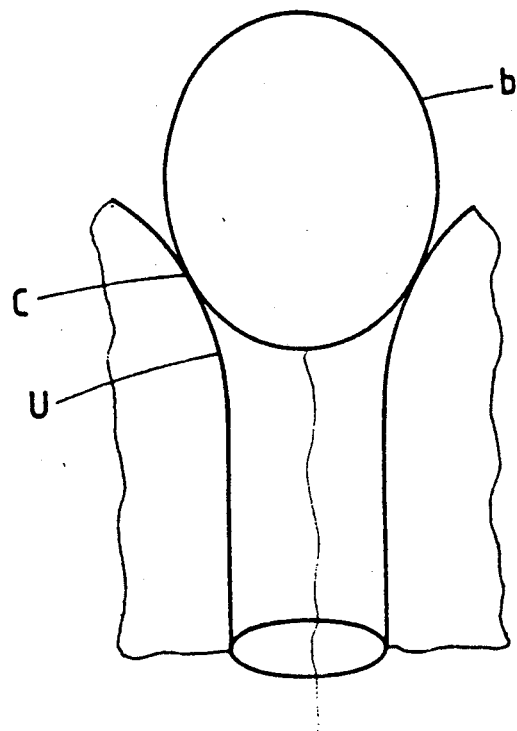
FIG. 3 is a diagram illustrating the prior art.

In FIG. 3 a balloon b is pulled onto the neck C of the bladder. The urethra U becomes deformed.

Figure 4:
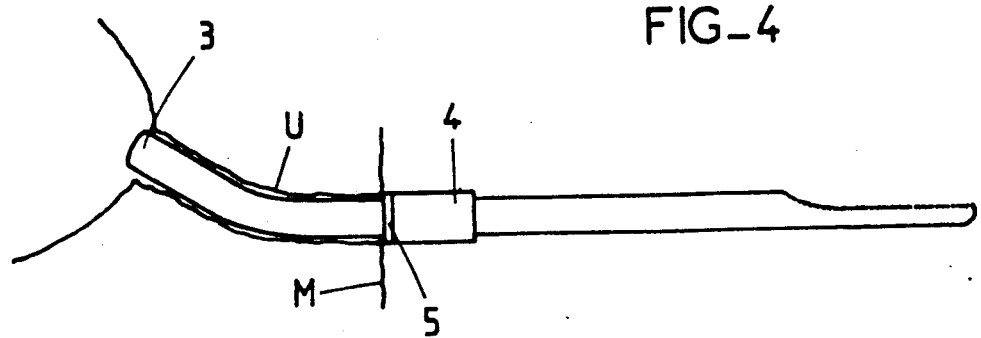
FIG. 4 is a diagram illustrating how the instrument according to the invention is used.

In FIG. 4, the instrument according to the invention is inserted into the urethra U over a distance given by the position of the cursor 4, the hilt 5 coming to bear against the meatus M. The urethra is not deformed. The angled end 3 accurately indicates the place where the restraining means must be fixed.

I claim:

1. An instrument for locating the proximal end of the urethra comprising:
   an elongated graduated measuring rod having two opposed flats;
   a cursor mounted so as to slide on the rod, said cursor comprising a hilt; and
   means for locking the cursor onto the rod;
   wherein at least one end of the rod is rigidly angled relative to a longitudinal axis of said rod.

2. Instrument according to claim 1, wherein the other end of the rod is shaped as a handle.

3. Instrument according to claim 1, in which the means for locking are constituted by the fact that the rod has such a shape that the cursor can slide on it only with a friction preventing it from moving by itself.

4. Instrument according to claim 1, wherein the means for locking comprise a screw device for locking of the cursor.

5. An instrument according to claim 1, wherein the length of said rod along said longitudinal axis is longer than the length of said rigidly angled end.

* * * * *